United States Patent [19]

Hall

[11] Patent Number: 4,477,660

[45] Date of Patent: Oct. 16, 1984

[54] 7-(S)-ACYLAMINOCEPHALOSPORIN SULFONES AND PROCESS

[75] Inventor: David A. Hall, Indianapolis, Ind.

[73] Assignee: Eli Lilly and Company, Indianapolis, Ind.

[21] Appl. No.: 442,077

[22] Filed: Nov. 16, 1982

[51] Int. Cl.³ .......................................... C07D 501/04
[52] U.S. Cl. ................................ 544/28; 260/239 A; 544/23; 544/30; 544/90; 548/218
[58] Field of Search ............................. 544/28, 30, 23

[56] References Cited

U.S. PATENT DOCUMENTS 4,399,131 8/1983 Durckheimer et al. .............. 544/28

OTHER PUBLICATIONS

Durckheimer et al., Royal Society of Chemistry Special Publication No. 38, Recent Advances in the Chemistry of β-Lactam Antibiotics, London, Chapter 4, pp. 46–51, (1981).

C. M. Pant and R. J. Stoodley, *J. Chem. Soc., Perkin Trans. I.*, 1978, pp. 1366–1369.

M. L. Sassiver and R. G. Shepard, *Tet. Letters*, pp. 3993–3996, (1969).

*Primary Examiner*—Paul M. Coughlan, Jr.
*Attorney, Agent, or Firm*—Paul C. Steinhardt; Arthur R. Whale

[57] ABSTRACT

This invention encompasses 7-(S)-acylamino-3-acetoxymethyl-3-cephem-4-carboxylic acid sulfones and the epimerization process for making them. The epimerization process employs an organic nitrogen base reagent having a pKa between about 9.0 to about 11.5. The compounds of this invention are intermediates in the synthesis of 1-oxa-β-lactam antibiotics.

40 Claims, No Drawings

7-(S)-ACYLAMINOCEPHALOSPORIN SULFONES AND PROCESS

SUMMARY OF THE INVENTION

This invention relates to 7-(S)-acylamino-3-acetoxymethyl-3-cephem-4-carboxylic acid sulfones ("7-(S)-acylaminocephalosporin sulfones"), the corresponding esters, and the process for the preparation thereof. The 7-(S)-acylaminocephalosporin sulfones have the following general formula 1:

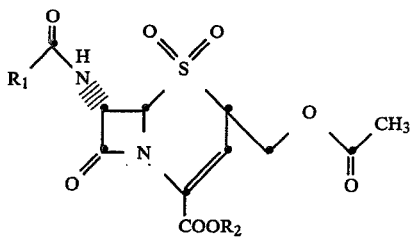

wherein $R_1$ is an alkyl, alkyloxy or aromatic group as defined below, e.g. benzyloxy, benzyl, phenyl, phenoxymethyl, chloromethyl, etc. and $R_2$ is hydrogen, sodium, potassium or an organic nitrogen base.

The process for making the above 7-(S)-acylaminocephalosporin sulfones of formula 1 involves reacting the corresponding 7-(R)-acylamino isomer with an organic nitrogen base that has a pKa between about 9.0 to about 11.5.

DETAILED DESCRIPTION OF THE INVENTION

One aspect of this invention encompasses 7-(S)-acylamino-3-acetoxymethyl-3-cephem-4-carboxylic acid sulfones ("7-(S)-acylaminocephalosporin sulfones") and the corresponding esters of the formula 1

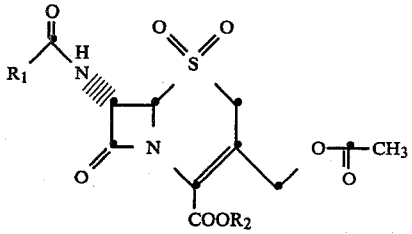

wherein $R_1$ is
a. $C_1$ to $C_7$ alkyl, $C_3$ to $C_7$ alkenyl, chloromethyl, dichloromethyl, 4-carboxybutyl, 4-formylbutyl, 4-substituted carboxybutyl, 4-amino-4-carboxybutyl, 4-protected amino-4-carboxybutyl, or 4-protected amino-4-substituted carboxybutyl; or
b. $C_1$ to $C_6$ alkoxy, $C_3$ to $C_6$ cycloalkoxy, benzyloxy or substituted benzyloxy, wherein the substituents are one to three groups chosen from the group consisting of $C_1$ to $C_4$ alkyl, $C_1$ to $C_4$ alkoxy, and chloro; or
c. 1,4-cyclohexadienyl, phenyl or substituted phenyl, wherein the substituents are one or two groups chosen from the group consisting of chlorine, bromine, hydroxy, protected hydroxy, trifluoromethyl, $C_1$ to $C_4$ alkyl, $C_1$ to $C_4$ alkoxy, carboxy, carboxymethyl, hydroxymethyl, aminomethyl, and protected aminomethyl; or
d. an arylalkyl group of the formula $$R'-(O)_m-CH_2-$$

wherein $R'$ is 1,4-cyclohexadienyl, phenyl or substituted phenyl as defined above, and m is zero or one; or
e. a substituted arylalkyl group of the formula

wherein $R''$ is $R'$ as defined above, 2-thienyl, or 3-thienyl; W is hydroxy or protected hydroxy, carboxy or protected carboxy, amino or protected amino; or
f. a heteroarylmethyl group of the formula $$R'''-CH_2-$$

wherein $R'''$ is 2-thienyl, 3-thienyl, 2-furyl, 3-furyl, 2-thiazolyl, 5-tetrazolyl or 1-tetrazolyl; and
$R_2$ is hydrogen, the conjugate acid of a nitrogen base that has a pKa between about 9.0 to about 11.5, sodium or potassium.

The second aspect of this invention encompasses the process for making 7-(S)-acylaminocephalosporin sulfones which comprises epimerizing a 7-(R)-acylamino-3-acetoxymethyl-3-cephem-4-carboxylic acid sulfone ("7-(R)-acylaminocephalosporin sulfone") of the formula 2

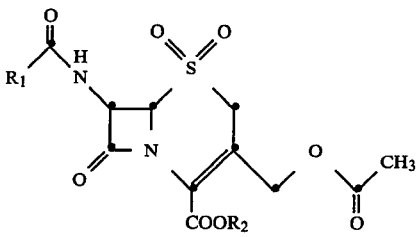

with a nitrogen base that has a pKa between about 9.0 to about 11.5, in water, adding a sufficient amount of the organic nitrogen base to keep the pH of the reaction mixture between about 9 to about 11.5, and maintaining the reaction temperature between about 0° C. to about 40°.

As used in the above formulas 1 and 2, the term "$C_1$ to $C_7$ alkyl" refers to methyl, ethyl, n-propyl, n-butyl, isobutyl, pentyl, n-hexyl, n-heptyl, cyclohexyl, and like aliphatic hydrocarbon chains. "$C_3$ to $C_7$ alkenyl" refers to the unsaturated hydrocarbon chains such as propenyl (allyl) butenyl, pentenyl, hexenyl, heptenyl, and the like. The term "$C_1$ to $C_6$ alkoxy" refers to groups such as methoxy, ethoxy, n-propoxy, iso-propoxy, n-butoxy, isobutoxy, valeroxy, hexyloxy, and the like.

The term "$C_3$ to $C_6$ cycloalkyloxy" refers to groups such as cyclopropoxy, cyclobutoxy, cyclopentyloxy and cyclohexyloxy.

The term "substituted benzyloxy" refers to compounds such as 3-chlorobenzyloxy, 2-methyl-3-chlorobenzyloxy, 2,4-dimethylbenzyloxy, 4-n-propylbenzyloxy, 4-n-butylbenzyloxy, 2-ethyl-4-n-propylbenzyloxy, 2-methoxybenzyloxy, 2,4-dimethoxybenzyloxy, 4-ethoxybenzyloxy, 3-chloro-4-ethoxybenzyloxy, 2-methyl-3-chlorobenzyloxy, 4-ethoxybenzyloxy, 4-t-butylbenzyloxy, 2,4-dichlorobenzyloxy, 2,3,4,-trimethoxybenzyloxy, 2,3,4-trimethylbenzyloxy, 3-propoxybenzyloxy, and the like.

The term "substituted phenyl" refers to a mono- or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3-chloro-4-bromophenyl, 2-fluorophenyl, and the like; a mono- or dihydroxyphenyl group such as 4-hydroxyphenyl, 3-hydroxyphenyl, 2,4-dihydroxyphenyl, and the like; a mono- or diprotected hydroxyphenyl group such as 4-protected hydroxyphenyl, 3-protected hydroxyphenyl, 2,4-diprotected hydroxyphenyl, and the like; a mono- or disubstituted lower alkylphenyl group such as 4-methylphenyl, 2,4-dimethylphenyl, 2-methylphenyl, 4-isopropylphenyl, 4-ethylphenyl, 3-n-propylphenyl, and the like; a mono- or disubstituted lower alkylphenyl ether for example, 2,6-dimethoxyphenyl, 4-methoxyphenyl, 3-ethoxyphenyl, 4-isopropoxyphenyl, 4-t-butoxyphenyl, and 3-ethoxy-4-methoxyphenyl; a mono- or disubstituted trifluoromethylphenyl group such as 4-trifluoromethylphenyl, 3,4-di-(trifluoromethyl)phenyl, and the like; a mono- or disubstituted carboxyphenyl group, such as 4-carboxyphenyl, 2-carboxyphenyl, 3-carboxyphenyl, 2,4-dicarboxyphenyl, and the like; a phenyl ring substituted by 1 or 2 carboxymethyl groups, such as 2-carboxymethylphenyl, 3-carboxymethylphenyl, 4-carboxymethylphenyl, 2,3-dicarboxymethylphenyl, and the like; a phenyl moiety that is mono or disubstituted by hydroxymethyl, resulting in benzyl alcohol type moieties, 2-(hydroxymethyl)phenyl, 4-(hydroxymethyl)phenyl, 3-(hydroxymethyl)phenyl, 3,4-di(hydroxymethyl)phenyl, and the like; phenyl groups mono or disubstituted by aminomethyl groups, resulting in benzylamine type moieties, e.g. 2-(aminomethyl)phenyl, 4-(aminomethyl)phenyl, 2,3-di(aminomethyl)phenyl, and the like. It should be noted that phenyl groups disubstituted with bromine are excluded from the above definition. The term "substituted phenyl" also represents disubstituted phenyl groups wherein substituents can be different, for example, 3-methyl-4-hydroxyphenyl, 3-chloro-4-hydroxyphenyl, 2-methoxy-4-bromophenyl, 4-ethyl-2-hydroxyphenyl, 2-hydroxy-4-chlorophenyl, 3-trifluoromethyl-4-hydroxyphenyl, 2-carboxy-4-ethoxyphenyl, 2-(aminomethyl)-4-(hydroxymethyl)phenyl, 4-carboxymethyl-2-methylphenyl, 3-(hydroxymethyl)-4-chlorophenyl, and like disubstituted phenyl groups bearing different substituents.

Illustrative of the acyl groups

when $R_1$ is a group of the formula $R'—(O)_m—CH_2—$, m is o and R' is 1,4-cyclohexadienyl, phenyl or substituted phenyl as defined above, are 2-(cyclohexa-1,4-dien-1-yl)acetyl, phenylacetyl, 4-chlorophenylacetyl, 3-hydroxyphenylacetyl, 4-hydroxy-3-methylphenylacetyl, 4-hydroxyphenylacetyl, 4-bromophenylacetyl, 4-ethoxyphenylacetyl, 3,4-dimethoxyphenylacetyl, and the like; and when m is 1, representative acyl groups are phenoxyacetyl, 3-hydroxyphenoxyacetyl, 4-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenoxyacetyl, 3,4-dimethylphenoxyacetyl, 4-isopropylphenoxyacetyl, 4-methyl-2-carboxyphenoxyacetyl, 4-aminomethylphenoxyacetyl, 4-carboxyphenoxyacetyl, 4-carboxymethylphenoxyacetyl, 3-trifluoromethylphenoxyacetyl, hydroxymethylphenoxyacetyl, aminophenoxyacetyl, and like acyl groups.

Illustrative of the acyl groups

wherein $R_1$ is a substituted arylalkyl group of the formula $$R''—\underset{\underset{W}{|}}{\overset{\overset{H}{|}}{C}}—$$

wherein R" is the same as R' defined above or 2-thienyl or 3-thienyl, are the hydroxy substituted arylalkyl groups such as the 2-hydroxy-2-phenylacetyl group of the formula

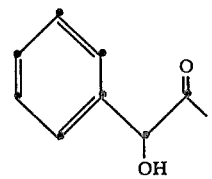

or the 2-(protected hydroxy)-2-phenylacetyl group of the formula

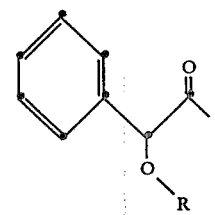

and similar groups wherein the phenyl ring is substituted, for example, 2-hydroxy-2-(4-methoxyphenyl)acetyl, 2-hydroxy-2-(3-chloro-4-hydroxyphenyl)acetyl, 2-hydroxy-2-(4-hydroxyphenyl)acetyl, 2-hydroxy-2-(3-bromophenyl)acetyl, 2-hydroxy-2-(3,5-dichloro-4-hydroxyphenyl)acetyl, 2-hydroxy-2-(3-chloro-4-methoxyphenyl)acetyl, 2-hydroxy-2-(3-chlorophenyl)acetyl and like groups; the 2-carboxy-2-phenylacetyl group or 2-(protected carboxy)-phenylacetyl group of the formula

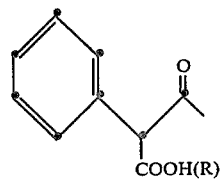

and similar groups wherein the phenyl ring is substituted, for example, 2-substituted carboxy-2-phenylacetyl, 2-carboxy-2-(4-chlorophenyl)acetyl, 2-carboxy-2-(4-methoxyphenyl)acetyl, 2-carboxy-2-(4-hydroxyphenyl)acetyl, and like groups, and the sodium, potassium and the organic nitrogen base salts thereof; the 2-amino-2-phenylacetyl or 2-(protected amino)-2-phenylacetyl of the formula

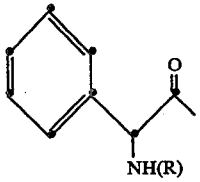

and similar groups wherein the phenyl ring is substituted, for example, 2-amino-2-phenylacetyl, 2-amino-2-(1,4-cyclohexadien-1-yl)acetyl, 2-amino-2-(4-hydroxyphenyl)acetyl, and like acyl groups.

Representative of the acyl groups

when $R_1$ is a heteroarylmethyl group of the formula $$R'''-CH_2-$$

wherein $R'''$ is 2-thienyl, 3-thienylacetyl, 2-furylacetyl, 3-furylacetyl, a 2-thiazolylacetyl group of the formula

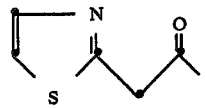

or a 2-(1-tetrazolyl)acetyl group of the formula

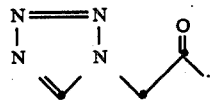

Exemplary of the compounds encompassed by this invention are:
sodium 7-(S)-[2-(fur-2-yl)acetamido]-3-acetoxymethyl-3-cephem-4-carboxylate sulfone,
potassium 7-(S)-[2-(tetrazol-1-yl]acetamido)-3-acetoxymethyl-3-cephem-4-carboxylate sulfone,
sodium 7-(S)-[2-amino-2-(4-hydroxyphenyl)acetamido]-3-acetoxymethyl-3-cephem-4-carboxylate sulfone,
potassium 7-(S)-[2-hydroxy-2-(3-chlorophenyl)acetamido]-3-acetoxymethyl-3-cephem-4-carboxylate sulfone,
sodium 7-(S)-[2-hydroxy-2-(4-hydroxyphenyl)acetamido]-3-acetoxymethyl-3-cephem-4-carboxylate sulfone,
potassium 7-(S)-(2-amino-2-phenylacetamido)-3-acetoxymethyl-3-cephem-4-carboxylate sulfone,
sodium 7-(S)-[2-amino-2-(4-hydroxyphenyl)acetamido]-3-acetoxymethyl-3-cephem-4-carboxylate sulfone,
sodium 7-(S)-(2-aminomethylphenylacetamido)-3-acetoxymethyl-3-cephem-4-carboxylate sulfone,
trimethylammonium 7-(S)-[2-(tetrazol-1-yl)acetamido]-3-acetoxymethyl-3-cephem-4-carboxylate sulfone,
piperazinium 7-(S)-[2-amino-2-(4-hydroxyphenyl)acetamido]-3-acetoxymethyl-3-cephem-4-carboxylate sulfone,
benzylammonium 7-(S)-[2-hydroxy-2-(3-chlorophenyl)acetamido]-3-acetoxymethyl-3-cephem-4-carboxylate sulfone,
cyclohexylammonium 7-(S)-[2-hydroxy-2-(4-hydroxyphenyl)acetamido]-3-acetoxymethyl-3-cephem-4-carboxylate sulfone,
diisopropylammonium 7-(S)-[2-amino-2-phenylacetamido]-3-acetoxymethyl-3-cephem-4-carboxylate sulfone,
n-butylammonium 7-(S)-[2-(n-butylammoniumcarboxylate)-2-(4-hydroxyphenyl)acetamido]-3-acetoxymethyl-3-cephem-4-carboxylate sulfone,
dimethylammonium 7-(S)-[(2-aminomethylphenyl)acetamido]-3-acetoxymethyl-3-cephem-4-carboxylate sulfone,
7-(S)-[2-(fur-2-yl)acetamido]-3-acetoxymethyl-3-cephem-4-carboxylic acid sulfone,
7-(S)-[2-(tetrazol-1-yl)acetamido]-3-acetoxymethyl-3-cephem-4-carboxylic acid sulfone,
7-(S)-[2-amino-2-(4-hydroxyphenyl)acetamido]-3-acetoxymethyl-3-cephem-4-carboxylic acid sulfone,
7-(S)-[2-hydroxy-2-(3-chlorophenyl)acetamido]-3-acetoxymethyl-3-cephem-4-carboxylic acid sulfone,
7-(S)-[2-hydroxy-2-(4-hydroxyphenyl)acetamido]-3-acetoxymethyl-3-cephem-4-carboxylic acid sulfone,
7-(S)-(2-amino-2-phenylacetamido)-3-acetoxymethyl-3-cephem-4-carboxylic acid sulfone,
7-(S)-(2-aminomethylphenylacetamido)-3-acetoxymethyl-3-cephem-4-carboxylic acid sulfone,
7-(S)-[2-(2,4-dichlorobenzyloxycarbonylamino)-2-(4-hydroxyphenyl)acetamido]-3-acetoxymethyl-3-cephem-4-carboxylic acid sulfone,
7-(S)-[2-(tetrahydropyranyloxy)-2-(3-chlorophenyl)acetamido]-3-acetoxymethyl-3-cephem-4-carboxylic acid sulfone,
sodium 7-(S)-[2-(2,4-dichlorobenzyloxycarbonylamino)-2-(4-hydroxyphenyl)acetamido]-3-acetoxymethyl-3-cephem-4-carboxylate sulfone,
sodium 7-(S)-[2-(tetrahydropyranyloxy)-2-(3-chlorophenyl)acetamido]-3-acetoxymethyl-3-cephem-4-carboxylate sulfone,
diethylammonium 7-(S)-[2-(2,4-dichlorobenzyloxycarbonylamino)-2-(4-hydroxyphenyl)acetamido]-3-acetoxymethyl-3-cephem-4-carboxylate sulfone, and
ethylammonium 7-(S)-[2-(tetrahydropyrinyloxy)-2-(3-chlorophenyl)acetamido]-3-acetoxymethyl-3-cephem-4-carboxylate sulfone.

Preferred compounds of this invention include:
triethylammonium 7-(S)-(p-toluylamido)-3-acetoxymethyl-3-cephem-4-carboxylate sulfone,
piperazinium 7-(S)-benzamido-3-acetoxymethyl-3-cephem-4-carboxylate sulfone,
triethylammonium 7-(S)-phenoxyacetamido-3-acetoxymethyl-3-cephem-4-carboxylate sulfone,
piperazinium 7-(S)-benzylcarbamato-3-acetoxymethyl-3-cephem-4-carboxylate sulfone,
triethylammonium 7-(S)-phenylacetamido-3-acetoxymethyl-3-cephem-4-carboxylate sulfone,
piperazinium 7-(S)-[2-(thien-2-yl)acetamido]-3-acetoxymethyl-3-cephem-4-carboxylate sulfone,
triethylammonium 7-(S)-[D-(5-(2,4-dichlorobenzyloxycarbonylamino))-5-(triethylammonium carboxylate)valeramido]-3-acetoxymethyl-3-cephem-4-carboxylate sulfone,
piperazinium 7-(S)-[D-(5-(2,4-dichlorobenzyloxycarbonylamino))-5-(piperazinium carboxylate)-valeramido]-3-acetoxymethyl-3-cephem-4-carboxylate sulfone,
potassium 7-(S)-(p-toluylamido)-3-acetoxymethyl-3-cephem-4-carboxylate sulfone,
potassium 7-(S)-benzamido-3-acetoxymethyl-3-cephem-4-carboxylate sulfone,
potassium 7-(S)-phenoxyacetamido-3-acetoxymethyl-3-cephem-4-carboxylate sulfone,
potassium 7-(S)-benzylcarbamato-3-acetoxymethyl-3-cephem-4-carboxylate sulfone,
potassium 7-(S)-phenylacetamido-3-acetoxymethyl-3-cephem-4-carboxylate sulfone,
potassium 7-(S)-[2-(thien-2-yl)acetamido]-3-acetoxymethyl-3-cephem-4-carboxylate sulfone,
potassium 7-(S)-[D-(5-(2,4-dichlorobenzyloxycarbonylamino))-5-(potassium carboxylate)valeramido[-3-acetoxymethyl-3-cephem-4-carboxylate sulfone,
sodium 7-(S)-[D-(5-(2,4-dichlorobenzyloxycarbonylamino))-5-(sodium carboxylate)valeramido]-3-acetoxymethyl-3-cephem-4-carboxylate sulfone,
7-(S)-(p-toluylamido)-3-acetoxymethyl-3-cephem-4-carboxylic acid sulfone,
sodium 7-(S)-benzamido-3-acetoxymethyl-3-cephem-4-carboxylate sulfone,
sodium 7-(S)-phenoxyacetamido-3-acetoxymethyl-3-cephem-4-carboxylate sulfone,
sodium 7-(S)-benzylcarbamido-3-acetoxymethyl-3-cephem-4-carboxylate sulfone,
sodium 7-(S)-phenylacetamido-3-acetoxymethyl-3-cephem-4-carboxylate sulfone,
sodium 7-(S)-[2-(thien-2-yl)acetamido]-3-acetoxymethyl-3-cephem-4-carboxylate sulfone, and
7-(S)-[D-(5-(2,4-dichlorobenzyloxycarbonylamino))-5-(carboxylic acid)valeramido]-3-acetoxymethyl-3-cephem-4-carboxylic acid sulfone.

The more preferred compounds of this invention include:
sodium 7-(S)-[D-(5-(2,4-dichlorobenzyloxycarbonylamino)-5-(sodium carboxylate)valeramido]-3-acetoxymethyl-3-cephem-4-carboxylate sulfone,
sodium 7-(S)-(p-toluylamido)-3-acetoxymethyl-3-cephem-4-carboxylate sulfone,
7-(S)-[2-(thien-2-yl)acetamido]-3-acetoxymethyl-3-cephem-4-carboxylic acid sulfone,
7-(S)-benzamido-3-acetoxymethyl-3-cephem-4-carboxylic acid sulfone,
7-(S)-phenoxyacetamido-3-acetoxymethyl-3-cephem-4-carboxylic acid sulfone,
7-(S)-benzylcarbamato-3-acetoxymethyl-3-cephem-4-carboxylic acid sulfone, and
7-(S)-phenylacetamido-3-acetoxymethyl-3-cephem-4-carboxylic acid sulfone.

In carrying out the epimerization process of this invention, an aqueous solution of the 7-(R)-acylamino cephalosporin sulfone in a soluble salt form is treated at a pH of between about 9.0 to about 11.5 with an organic nitrogen base having a pKa of between about 9 and about 11.5.

The soluble salt form of the 7-(R)-acylamino cephalosporin sulfone can be the sodium or potassium salt or the salt formed with the organic nitrogen base. Examples of such organic nitrogen base salts are those formed with triethylamine, piperizane, cyclohexylamine and benzylamine.

The solution of the 7-(R)-acylamino cephalosporin sulfone can be prepared by adding the desired sodium or potassium base, such as sodium hydroxide or potassium hydroxide, to an aqueous slurry of the free acid form of the sulfone. Alternatively, the slurry of the sulfone acid can be treated with the desired organic nitrogen base to form the soluble salt.

The aqueous solution of the 7-(R)-acylamino cephalosporin sulfone thus obtained is then treated with the epimerizing organic nitrogen base while the pH of the resultant solution is maintained between about 9.0 to about 11.5. It will be understood by those skilled in the art that the aqueous slurry of the 7-(R)-acylamino cephalosporin sulfone free acid can be treated with sufficient organic nitrogen base to first form the soluble salt of the sulfone acid and secondly to effect the epimerization at the 7-position of the molecule.

Preferred organic nitrogen bases are benzylamine, piperazine, trimethylamine, ethylenediamine, methylamine, cyclohexylamine, dimethylamine, n-butylamine, ethylamine, triethylamine, diethylamine, diisopropylamine, or hexamethylenediamine. The more preferred nitrogen bases are piperazine and triethylamine.

The amount of nitrogen base added to either the aqueous slurry or aqueous solution of 7-(R)-cephalosporin sulfone starting material is that amount sufficient to maintain the pH of the resulting solution between about 9.0 to about 11.5. The preferred pH range is between about 9.5 to about 10.5. The preferred method of maintaining the pH of the reaction solution between about 9.0 to about 11.5 comprises the use of two molar equivalents of organic nitrogen base per molar equivalent of 7-(R)-acylaminocephalosporin sulfone with buffering of the resultant reaction solution at the desired pH with a suitable base, e.g., by periodic additions of 5N sodium hydroxide solution. It should be noted that the organic nitrogen base can be added as a solid or as an aqueous solution to the starting material-containing slurry or aqueous solution.

The time required for the epimerization process is usually determined by monitoring the reaction with high performance liquid chromatographic analysis until the analysis shows that the 7β-starting material is essentially gone.

Typically the epimerization process can take up to about 1 hour, although the reaction is often complete in a few minutes.

The temperature range for the epimerization process is between about 0° C. to about 40° C. The preferred temperature range is ambient temperature, i.e., 15° C. to 25° C.

The 7-(S)-acylaminocephalosporin sulfone product is isolated by decreasing the pH of the reaction solution to 7.0 or below. The pH of the reaction mixture is usually decreased to between about 2 to about 3 by the addition of a strong acid such as hydrochloric acid or sulfuric acid. The 7-(S)-acylaminocephalosporin sulfone product as the free acid is extracted into a water-immiscible organic solvent such as ethyl acetate. The ethyl acetate can be added to the reaction mixture either before or after the addition of the acid.

For purposes of the process of this invention, hydroxy and amino groups need not be protected. It may be desirable to protect these groups for the purposes of the reactions following the instant process, as described below. Therefore, when the term "protected amino" is used in this specification, it refers to amino protecting groups known to be suitable amino protecting groups in the cephalosporin art, and in addition, groups which will survive the conditions of the epimerization reaction of the instant application. Amino protecting groups suitable in the cephalosporin art are groups that are removable without disrupting the remainder of the cephalosporin molecule. Examples of such amino protecting groups include the t-butoxycarbonyl group, the benzyloxycarbonyl group, the 2,4-dichlorobenzyloxycarbonyl group and like amino protecting groups. A preferred amino protecting group is the 2,4-dichlorobenzyloxycarbonyl group.

As with the amino protecting groups, the term "protected hydroxy" refers to groups known to be suitable in the cephalosporin art and which are stable to the conditions of the instant epimerization. Examples of such groups include the formyloxy group, the chloroacetoxy group, the benzhydryloxy group, and the like.

In the above definitions, the terms "protected hydroxy" and "protected amino" are not exhaustively defined. Many such protecting groups are well known in the cephalosporin art and the use of other groups equally applicable to the epimerization process of this invention, such as those described in J. F. W. McOmie, "Protective Groups in Organic Chemistry," Plenum Press, New York, 1973 or T. W. Greene, "Protective Groups in Organic Synthesis," Wiley-Interscience, New York, 1981, will be recognized as suitable. Thus, there is no novelty or inventiveness asserted with regard to the "protected" terms discussed above.

As used in this application, the term "substituted carboxy" means carboxy acid salt. The cation of this salt is sodium or potassium ion, or the cation of an organic nitrogen base having a pKa from between about 9 to about 11.5. These substituted carboxy groups arise from the dissolution and/or epimerization of the process of this invention.

The preferred 7-(R)-cephalosporin sulfone starting materials for the epimerization process of this invention are:
triethylammonium 7-(R)-(p-toluylamido)-3-acetoxymethyl-3-cephem-4-carboxylate sulfone,
piperazinium 7-(R)-benzamido-3-acetoxymethyl-3-cephem-4-carboxylate sulfone,
triethylammonium 7-(R)-phenoxyacetamido-3-acetoxymethyl-3-cephem-4-carboxylate sulfone,
piperazinium 7-(R)-benzylcarbamato-3-acetoxymethyl-3-cephem-4-carboxylate sulfone,
triethylammonium 7-(R)-phenylacetamido-3-acetoxymethyl-3-cephem-4-carboxylate sulfone,
piperazinium 7-(R)-[2-(thien-2-yl)acetamido]-3-acetoxymethyl-3-cephem-4-carboxylate sulfone,
triethylammonium 7-(R)-[D-(5-(2,4-dichlorobenzyloxycarbonylamino))-5-(triethylammonium carboxylate)valeramido]-3-acetoxymethyl-3-cephem-4-carboxylate sulfone,
piperazinium 7-(R)-[D-(5-(2,4-dichlorobenzyloxycarbonylamino))-5-(piperazinium carboxylate)valeramido]-3-acetoxymethyl-3-cephem-4-carboxylate sulfone,
potassium 7-(R)-(p-toluylamido)-3-acetoxymethyl-3-cephem-4-carboxylate sulfone,
potassium 7-(R)-benzamido-3-acetoxymethyl-3-cephem-4-carboxylate sulfone,
potassium 7-(R)-phenoxyacetamido-3-acetoxymethyl-3-cephem-4-carboxylate sulfone,
potassium 7-(R)-benzylcarbamato-3-acetoxymethyl-3-cephem-4-carboxylate sulfone,
potassium 7-(R)-phenylacetamido-3-acetoxymethyl-3-cephem-4-carboxylate sulfone,
potassium 7-(R)-[2-(thien-2-yl)acetamido]-3-acetoxymethyl-3-cephem-4-carboxylate sulfone,
potassium 7-(R)-[D-(5-(2,4-dichlorobenzyloxycarbonylamino)-5-(potassium carboxylate)valeramido]-3-acetoxymethyl-3-cephem-4-carboxylate sulfone,
sodium 7-(R)-[D-(5-(2,4-dichlorobenzyloxycarbonylamino))-5-(benzhydryl carboxylate)valeramido]-3-acetoxymethyl-3-cephem-4-carboxylate sulfone,
7-(R)-(p-toluylamido)-3-acetoxymethyl-3-cephem-4-carboxylic acid sulfone,
sodium 7-(R)-benzamido-3-acetoxymethyl-3-cephem-4-carboxylate sulfone,
sodium 7-(R)-phenoxyacetamido-3-acetoxymethyl-3-cephem-4-carboxylate sulfone,
sodium 7-(R)-benzylcarbamato-3-acetoxymethyl-3-cephem-4-carboxylate sulfone,
sodium 7-(R)-phenylacetamido-3-acetoxymethyl-3-cephem-4-carboxylate sulfone,
sodium 7-(R)-[2-(thien-2-yl)acetamido]-3-acetoxymethyl-3-cephem-4-carboxylate sulfone,
7-(R)-[D-(5-(2,4-dichlorobenzyloxycarbonylamino)-5-(carboxylic acid)valeramido]-3-acetoxymethyl-3-cephem-4-carboxylic acid sulfone, and
7-(R)-[D-(5-(2,4-dichlorobenzyloxycarbonylamino))-5-(carboxylic acid)valeramido]-3-acetoxymethyl-3-cephem-4-carboxylic acid sulfone.

The more preferred 7-(R)-acylaminocephalosporin sulfones for use in the epimerization process of this invention are
7-(R)-[D-(5-(2,4-dichlorobenzyloxycarbonylamino)-5-(carboxylic acid)valeramido]-3-acetoxymethyl-3-cephem-4-carboxylic acid sulfone,
7-(R)-(p-toluylamido)-3-acetoxymethyl-3-cephem-4-carboxylic acid sulfone,
7-(R)-[2-(thien-2-yl)acetamido]-3-acetoxymethyl-3-cephem-4-carboxylic acid sulfone,
triethylammonium 7-(R)-[2-(thien-2-yl)acetamido]-3-acetoxymethyl-3-cephem4-carboxylate sulfone,
7-(R)-benzamido-3-acetoxymethyl-3-cephem-4-carboxylic acid sulfone,
7-(R)-phenoxyacetamido-3-acetoxymethyl-3-cephem-4-carboxylic acid sulfone,
7-(R)-benzylcarbamato-3-acetoxymethyl-3-cephem-4-carboxylic acid sulfone, and
7-(R)-phenylacetamido-3-acetoxymethyl-3-cephem-4-carboxylic acid sulfone.

The 7-(S)-acylamino cephalosporin sulfones of the instant invention are converted to 1-oxa β-lactam antibiotics by the series of reactions as follows. The 7-(S)-acylaminocephalosporin sulfones of this invention are deacylated to the corresponding 3-hydroxymethyl compound by using immobilized citrus acetyl esterase, and the 3-hydroxymethyl compound is electrolytically reduced to a 2-(R)-sulfinic acid azetidinone compound. Depending on the type of acylamino side chain that is bonded to the 2-(R)-sulfinic acid azetidinone, the 2-(R)-sulfinic acid is then oxidized either to an epi-oxazoline compound or a 7-(S)-acylamino 3-methyl 1-oxa β-lactam compound. This series of reactions is diagrammed in Scheme 1.

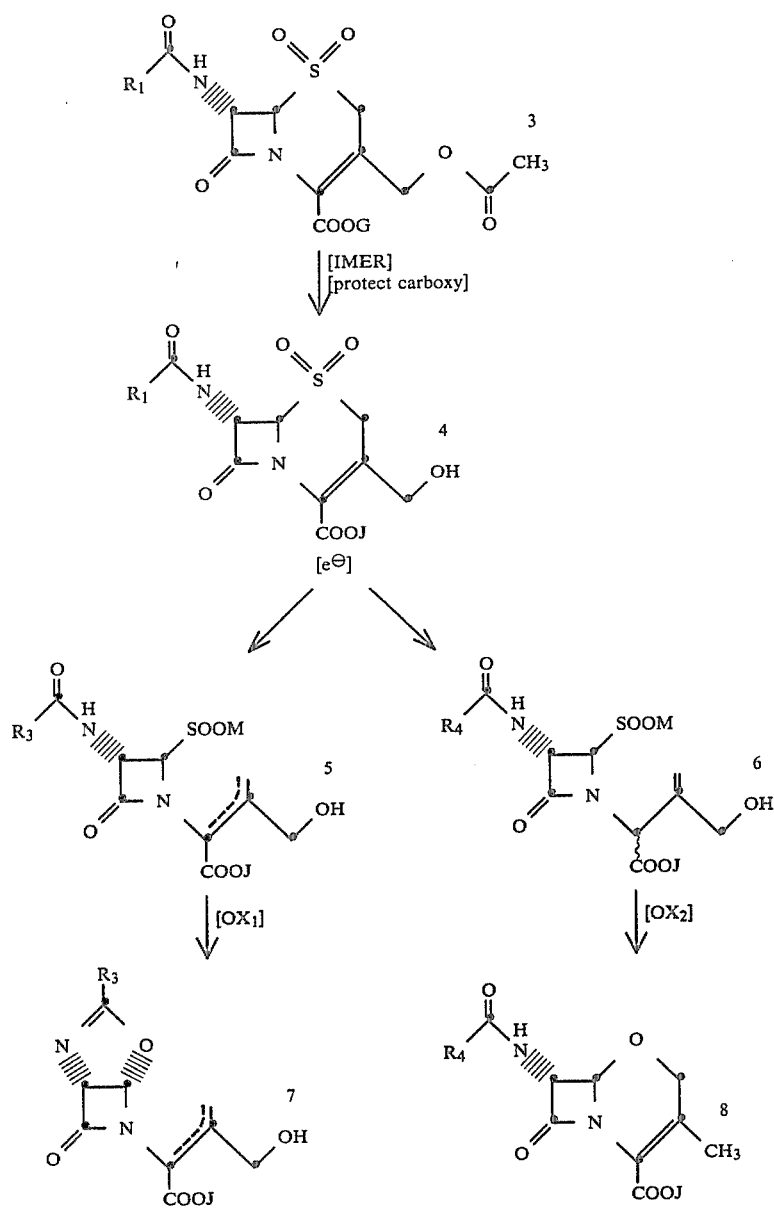

In the above Scheme 1, $R_1$ has the same meaning as defined for formula 1 and G is an alkali metal cation. $R_3$ is the same as $R_1$, except that it excludes the $C_1$ to $C_6$ alkoxy, $C_3$ to $C_6$ cycloalkoxy, benzyloxy or substituted benzyloxy groups. $R_4$ includes only $C_1$ to $C_6$ alkoxy, $C_3$ to $C_6$ cycloalkoxy, benzyloxy or substituted benzyloxy as defined for formula 1. The symbol "J" indicates a carboxylic acid salt or protecting group that will survive the electrolysis reaction conditions, i.e., one that is not easily reduced. This requirement rules out protecting groups such as p-nitrobenzyl, 2,2,2-trichloroethyl, 2,2,2-tribromoethyl, 2,2-dibromoethyl, 2-iodoethyl, 2,2-iodoethyl, 2,2-diiodomethyl, 2,2,2-triiodomethyl, and like protecting groups having nitro, activated halogeno or cyano substituents. The carboxy protecting groups used also must not be so acid-labile so as to be removed by the proton source used during the electrolysis reaction, e.g. when the proton source is the carboxylic acid having a pKa between about 0 to about 5. Acid-labile protecting groups that should be avoided are the silyl groups such as trimethylsilyl. If these limitations are heeded, carboxy protecting groups that can be used in the electrolysis process are commonly used carboxylic acid protecting groups in the cephalosporin art such as tert-butyl, benzyl, diphenylmethyl (benzhydryl), 4-methoxybenzyl, $C_2$-$C_6$ alkanoyloxymethyl, phenacyl, chlorophenylacyl, dimethylallyl, and the like. Preferred carboxylic acid protecting groups are benzhydryl, 4-methoxybenzyl and tert-butyl.

The symbol "IMER" in the above Scheme 1 stands for immobilized enzyme reactor. In this instance, the enzyme is citrus esterase, and the enzyme catalyzes the deacetylation of the 3-acetoxymethyl compound of formula 3 to the 3-hydroxymethyl compound of formula 4.

The deacylation is preferably carried out with the esterase immobilized on a modified silica gel. This modified silica gel is prepared using silica gel of 70-230 mesh and 62-200μ particle size (i.e. Fractosil 200, E. Merck and Co.) and cleaning the silica gel by first deaerating the slurry of the silica in aqueous 10% nitric acid, heating for 3 hours at about 80° C. and then rinsing with water. The clean silica gel is then slurried in 10% 3-aminopropyltriethoxysilane and the slurry is deaerated under vacuum. The pH is adjusted to between 3 and 4 with dilute hydrochloric acid and the slurry agitated periodically while heating at 80° C. for 3 hours. This modified silica is collected by filtration, washed with water, and dried for 16 hours at 105° C. The dried modified silica is slurried with an aqueous 3% glutaraldeayde solution buffered by pH 7 phosphate (5-10 vol./wt. of silica). The slurry is periodically agitated during 3 hours and is then washed with water at pH 7 citrate buffer.

A neutral aqueus solution of the acetyl esterase is added to the aldehyde-silica and allowed to interact for about 20 hours. The silica-enzyme complex is then transferred to a glass column and washed with pH 7 citric acid buffer.

The 3-acetoxymethyl cephalosporin sulfone (formula 3) is dissolved in 0.2M aqueous sodium citrate and the pH of the solution is adjusted to 7 with 1M sodium hydroxide. The solution is then passed over the silica-enzyme column. Ethyl acetate is added to the effluent and the mixture is chilled to 0° C. The pH of the cold mixture is adjusted to 2.5 with hydrochloric acid and the ethyl acetate layer is separated. The acidified aqueous phase is extracted further with ethyl acetate and all extracts are combined and are washed with acidified brine and dried.

As indicated in the above Scheme 1 by the term "protect carboxy," it is preferred to protect the carboxy groups of the 3-hydroxymethyl cephalosporin sulfone product compound (formula 4) before these compounds are subjected to the next step, i.e. the electrolysis process. One method of protecting the carboxy group is to concentrate the washed and dried extract from the IMER in vacuo and then to add to the concentrate the esterifying agent. For example, the concentrate can be treated with diphenyldiazomethane to form diphenylmethyl 7-(S)-acylamino-3-hydroxymethyl-3-cephem-4-carboxylate sulfone.

Preferably, the esterification of the 3-hydroxymethyl sulfone acid is carried out by adding an ethyl acetate solution containing a stoichiometric amount of diphenyldiazomethane to the effluent of the column. This preferred route of esterification diminishes the amount of lactone formed with the 3-hydroxymethyl group and the free carboxy group by intramolecular esterification.

A second method for protecting the carboxy groups of the 3-hydroxymethyl sulfone acid is simply by neutralizing them with a base such as sodium acetate or sodium hexanoate.

This deacetylation process using an immobilized enzyme is further described in copending U.S. application Ser. No. 442,078, filed this even date.

The 3-hydroxymethyl protected-carboxy compounds of formula 5 are then electrolytically reduced, as indicated by the term "e⊖" in Scheme 1, by the process described in U.S. Pat. Ser. No. 4,436,596, filed this even date and in copending U.S. application No. 560,283, filed Dec. 12, 1983. The products of this electrolysis are 2-(R)-sulfinic acid azetidinone compounds, formulas 5 and 6 above. This process comprises electrolytically reducing at a potential above the reduction potential required for the cleavage of the sulfone-to-$C_2$ bond of the 3-hydroxymethyl compound of formula 4 in a liquid medium comprised of a polar organic solvent, water, or a mixture of the two, all of which are stable under the conditions of the electrolysis, and (a) when the medium used is a polar organic solvent or a mixture of water and a polar organic solvent, a proton source comprised of a carboxylic acid having a pKa between about zero to about five in an amount equal to at least one molar equivalents per molar equivalent of cephalosporin sulfone; or (b) when the medium used is water, maintaining the pH of the aqueous medium between about three to about nine; at a temperature above the freezing point of the liquid medium used to about 40° C.; wherein the electrolytic reduction is carried out in the presence of an electrolyte selected from the group consisting of an alkali metal salt, ammonium and substituted ammonium salts.

More significantly, the electrolysis cells used in the electrolysis are the conventional types now known in the electrochemical art. The cells used are divided into compartments, so that each of the electrodes is immersed in fluid which is physically separated from the fluids of the other compartments, but is electrically connected to them. Cathodes that are used are made from graphite, mercury, copper, lead, zinc or cadmium. The composition of the anode, since it does not participate in the reductive process, is not critical. For this process the anode can be made of platinum of carbon.

The solvent used in the cathode compartment can be water, a polar organic solvent or a mixture of water and organic solvent when the polar organic solvent is water-miscible. The major limitation on the type of organic solvents that can be used are ones that are not reduced at a less negative potential than the starting material. The polar organic solvent used in the process should have a high dielectric constant and should possess no nitro functional groups on the molecule. Suitable polar organic solvents include dimethylformamide, acetonitrile, formamide, acetamide, methanol, ethanol, isopropanol, tetrahydrofuran, acetone, N-methylformamide, and N-benzylnitrile. Preferred polar organic solvents are methanol and dimethylformamide.

The salts that are dissolved in the above solvent to form the catholyte of the process are lithium, sodium, potassium, ammonium and substituted ammonium salts. Preferred salts for use as catholytes in the electrolysis process include sodium perchlorate, sodium sulfate, sodium acetate, sodium chloride, lithium chloride, and tetraethylammonium perchlorate.

The electrolysis also requires the presence of a proton source, which must be present in the catholyte in a concentration of at least one molar equivalent per molar equivalent of the 3-hydroxymethyl cephalosporin sulfone starting material.

The proton source used will depend on whether the solvent system is organic, a mixture of organic and water, or simply water. For a solvent system in the catholyte which is organic or a mixture of organic and water, the proton source should be a low molecular weight carboxylic acid having a pKa between about 0 to about 5. Examples of such a proton source include acetic acid, formic acid, 2-chloroacetic acid, 2,2-dichloroacetic acid, benzoic acid, 2,2,2-trifluoroacetic acid, and 2-phenylthioacetic acid. When water is used as the solvent for the catholyte, the catholyte salt is dissolved in water to give a pH of between about 3 to about 9 and the substrate cephalosporin sulfone is added while the pH is maintained at between about 3 to about 9 by the periodic addition of a mineral acid such as hydrochloric acid or sulfuric acid. The preferred catholyte salt/proton source combinations for this invention are sodium sulfate/sulfuric acid and sodium chloride/hydrochloric acid.

The dividers typically used for the electrolysis are made from cation exchange membranes, e.g., perfluorosulfonic acid cation exchange membranes sold by E. I. Dupont de Nemours and Co., Wilmington, Delaware, under the trade name Nafion.

Since the anode occupies a cell compartment by itself, it is immersed in a conductive fluid. If the divider is a porous membrane, it is advisable to provide an anode fluid which is compatible with the catholyte, such as an aqueous solution of the mineral acid used in the catholyte. If the cell divider is porous only to ions, then the anolyte may be any convenient conductive fluid, such as dilute aqueous solutions of ionizable salts and acid. A preferred anolyte is an aqueous solution of phosphate buffer at pH 2.3.

The potential of the electrolysis process, of course, depends on the condition of the dividing membrane, concentration of the proton source and the catholyte, and the concentration of the compound to be reduced in the catholyte. It has been observed, however, that the potential of the cathode for reductions according to this process is from about $-1.0$ volt to about $-1.9$ volts relative to a saturated calomel reference electrode. The highest negative potential usable for this process would be at the degradation potential of the solvent.

The reduction can be carried out in a constant potential mode, as detailed above, or on a constant current basis, where the preferred current range is betweeen about 2 to about 200 ma/cm$^2$.

The progress of the electrolysis process is monitored by high performance liquid chromatography analysis of the reaction mixture.

The preferred temperature range for the process is between about $-10°$ C. to about 10° C.

The concentration of the compound to be reduced is widely variable and is limited only by the solubility of the compound in the catholyte. Of course, it is most economical to use relatively high concentrations, in order to obtain the maximum effectiveness from the solvents used in the process. However, isolation of the product from the catholyte is frequently more difficult when high concentrations of starting material are used.

The typical work-up procedure following the electrolysis process involves removing the catholyte from the cathode compartment, adding a 0.3 M pH 7 1:1 phosphate:saturated sodium chloride solution to the catholyte, extracting the resultant solution with ethyl acetate, and washing the ethyl acetate extracts with the above phosphate:sodium chloride buffer again. The ethyl acetate extracts are dried over magnesium sulfate, filtered, the ethyl acetate is removed and the product obtained as a foam is purified by high performance liquid chromatography.

In an alternative isolation procedure the catholyte is removed from the cathode compartment, ethyl acetate is added to the catholyte, which is then acidified with 12 N sulfuric acid until the pH of the aqueous layer is 2.5. The ethyl acetate layer is then separated, evaporated and the resultant product is taken up again in ethyl acetate and recrystallized.

Finally, if there is no desire to isolate the product azetidinone sulfinic acid compounds, the catholyte can be removed from the cathode compartment and used as is in the subsequent oxidation steps as described below.

The 3-(S)-acylamino-2-(R)-sulfinic acid azetidinone compounds of formula 5 above are then converted to the epi-oxazoline compounds of the formula 7. The oxidation process that effects this conversion, represented by the symbol "ox" in Scheme 1, is carried out by mixing at least one molar equivalent and up to about 1.5 molar equivalents of the oxidizing agent with each molar equivalent of the 2-(R)-sulfinic acid azetidinone compound. An even larger excess of the oxidizing agent can be employed; however, no advantage is gained thereby. Preferably, therefore, the ratio of reactants is from about 1.0 to about 1.1 molar equivalents of oxidizing agent per molar equivalent of the 2-(R)-sulfinic acid azetidinone compound. Preferably, the resulting mixture is dissolved in a suitable inert organic solvent and this reaction mixture is maintained at temperature from about 0° C. to about 30° C., for a period sufficient for the completion of the reaction. This oxidation reaction can be carried out on a 2-(R)-sulfinic acid azetidinone compound that has been isolated and/or purified, or the oxidizing agent can be added directly to the catholyte after it has been removed from the cathode compartment.

The oxidizing agent used in this reaction can be any of a wide range of such agents. Typical agents include, for example, lead (IV) compounds such as lead tetraacetate, lead oxide, and the like; manganese (IV) compounds, such as manganese acetoacetonate, manganese oxide, and the like; sodium hypochlorite; N-haloimides, such as N-bromosuccinimide, and the like; ammonium cerium nitrate; and other like compounds. Preferably, the oxidizing agent is a lead (IV) compound, in particular, lead tetraacetate, or an N-bromoimide, in particular, N-bromosuccinimide.

The oxidation process is preferably carried out in an organic solvent which, under the conditions of the epi-oxazoline formation, does not appreciably react either with the reactants or with the products. Suitable inert organic solvents include, for example, aromatic hydrocarbons, such as benzene, toluene, ethylbenzene, cumene, and the like; halogenated hydrocarbons, such as carbon tetrachloride, chlorobenzene, bromoform, bromobenzene, methylene chloride, ethylene chloride, 1,1,2-trichloroethane, ethylene dibromide, and the like; amides, such as N,N-dimethylformamide, and the like; alcohols, such as methanol, ethanol, and the like; esters, such as ethyl acetate, and the like; nitriles, such as acetonitrile, and the like; and the other appropriate inert solvents. Preferred solvents include N,N-dimethylformamide, methanol, acetonitrile, ethylacetate, methylene chloride, and the like.

The temperature of the oxidation reaction generally is from about 0° C. to about 30° C. Preferably, the reaction temperature is at the lower end of this range, generally from about 0° C. to about 5° C.

Typically the oxidation reaction is complete in a very short time, generally in a matter of a few minutes. However, the time of the reaction can be greatly extended, for example, to several hours, without detrimental effects. Normally the time of the reaction will be no longer than about 1 hour.

The epi-oxazoline compounds are isolated by methods well known in the art. Specific procedures therefor are found in the Examples below.

The above oxidation reaction is more fully described and claimed in W. A. Spitzer, U.S. application Ser. No. 442,052, filed this even date.

As noted above, the epi-oxazoline compounds of formula 7 produced by this oxidation process are useful intermediates in the production of 1-oxa β-lactam antibiotics. The process for the these conversions are found in T. Tsuji et al., U.S. Pat. No. 4,220,766, issued Sept. 2, 1980, and T. Tsuji et al., U.S. Pat. Nos. 4,271,295 and 4,271,296, issued June 2, 1981, herein incorporated by reference.

The 3-(S)-carbamato-2-(R)-sulfinic acid azetidinone compounds of formula 6 above are converted to the 7-(S)-carbamato 3-methyl 1-oxa β-lactam compounds of formula 8 above by an oxidation process represented by the symbol "ox$_2$" in the above Scheme 1. This oxidation reaction involves reacting the 2-(R)-sulfinic acid azetidinone compounds of formula 6 above with lead tetraacetate in liquid sulfur dioxide containing copper (II) ion to provide an isomeric mixture of a cyclization product, i.e., a 3-exomethylene 1-oxo β-lactam compound of the formula

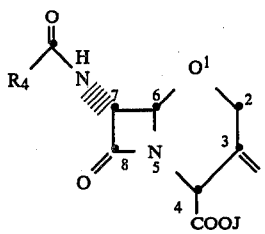

and a 3-methyl 1-oxa β-lactam compound of the formula

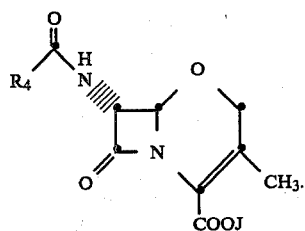

This process proceeds without production of the epioxazoline compound, and is carried out in an inert organic solvent at a temperature between about −25° C. to about 10° C. with between about 1.0 to about 2.5 molar equivalents of lead tetraacetate per molar equivalent of azetidinone sulfinic acid compound starting material.

The amount of sulfur dioxide used can be between about 1 to about 3 molar equivalents per molar equivalent of substrate azetidinone compound, preferably in excess of the molar equivalents of substrate compound used. The sulfur dioxide can be used as a solvent by itself or in addition to an inert organic solvent such as ethyl acetate, methylene chloride, tetrahydrofuran, dioxane, and the like.

Copper (II) ion is readily available as copper sulfate, employing between about 10 to about 15 mg of copper sulfate per millimole of azetidinone sulfinic acid compound.

The reaction is carried out by adding lead tetraacetate and copper sulfate to a solution of the azetidinone sulfinic acid (formula 6) in liquid sulfur. The reaction mixture is stirred from about 20 minutes to about 30 minutes.

Alternatively, the reaction can be carried out in an inert organic solvent using lead tetraacetate without the presence of sulfur dioxide or copper (II).

The 3-exomethylene 1-oxa β-lactam compound can be easily isomerized to the 3-methyl 1-oxa β-lactam compound in the presence of a base such as triethylamine. The 3-methyl 1-oxa β-lactam compounds are intermediates in the synthesis of 1-oxa β-lactam antibiotic compounds, such as those described in U.S. Pat. Nos. 4,226,866 and 4,138,486.

The above cyclization reaction of the azetidinone sulfonic acid compound to the 1-oxa β-lactam intermediates is described in D. A. Hall, U.S. application Ser. No. 442,080, filed this even date. The conversion of the 1-oxa β-lactam intermediate produced in this cyclization process to the 1-oxa β-lactam antibiotic compounds is described in the above copending U.S. application of D. A. Hall. Further examples of this conversion are found in B. G. Christensen et al., U.S. Pat. No. 4,226,866, issued Oct. 7, 1980, and Narisada et al., U.S. Pat. No. 4,138,486, issued Feb. 6, 1979, both of which are herein incorporated by reference.

The 7-(R)-cephalosporin sulfones used as the starting material for the epimerization process of this invention are prepared by oxidation of the corresponding cephalosporin sulfide to a sulfone. This oxidation is best carried out in an aqueous reaction medium maintained at a pH between about 5.0 and about 6.0 with an excess of potassium hydrogen persulfate. The oxidation proceeds well at temperatures between about 15° C. to about 45° C. The sulfone is recovered from the aqueous reaction mixture by acidifying the mixture to form the free sulfone carboxylic acid and extraction of the latter acidified aqueous reaction mixture with a suitable water immiscible solvent such as ethyl acetate. This process is described in copending U.S. application Ser. No. 442,079, filed this even date.

The following Examples are supplied to further illustrate the invention, and are not meant to limit the scope in any fashion.

EXAMPLE 1

7-(S)-[D-(5-(2,4-Dichlorobenzoylamino)-5-(carboxylic acid)valeramido]-3-acetoxymethyl-3-cephem-4-carboxylic acid sulfone A. Oxidation 7-(R)-[D-(5-(2,4-Dichlorobenzoylamino))-5-(carboxylic acid)valeramido]-3-acetoxymethyl-3-cephem-4-carboxylic acid (44.1 g, 75 mm) was suspended in water (400 ml), and sodium bicarbonate and octanol (to prevent foaming) were added to the suspension with stirring. A solution with a pH of 7.0 was obtained. Potassium hydrogen persulfate (Oxone ™, 92.1 g, 150 mm), was dissolved in water (400 ml) and the pH of the resultant solution was adjusted to 2.5 by the addition of 5N sodium hydroxide. The aqueous Oxone solution was added slowly to the aqueous cephalosporin solution while maintaining the pH of the solution at 5.7 between additions of the Oxone solution with the addition of a saturated aqueous solution of sodium bicarbonate. HPLC analysis showed the reaction to be complete in 1 h. At this point, the starting cephalosporin had been converted to 7-(S)-[D-(5-(2,4-dichlorobenzoylamino))-5-(carboxylic acid)valeramido]-3-acetoxymethyl-3-cephem-4-carboxylic acid sulfone.

B. Epimerization

Sodium bisulfite (7.5 g) was added to the above reaction mixture to neutralize excess Oxone. The pH of the solution was adjusted to 6.0 by the addition of 5N aqueous sodium hydroxide solution. Piperazine (12.48 g, 150 mm) was added and the pH of the resultant solution was adjusted to 9.0 by the addition of aqueous 5N sodium hydroxide solution. The pH of the solution was maintained at 9.0 during the course of the reaction by additional portions of aqueous 5N sodium hydroxide solution. HPLC analysis of the reaction mixture showed the reaction to be complete after 0.75 h. The reaction mixture was then chilled to 20° C. and the pH of the solution was adjusted to 2.5 with 12N sulfuric acid. The reaction mixture was then extracted with ethyl acetate (600 ml, 2×). The ethyl acetate extracts were combined and washed with an aqueous solution of 0.1N hydrochloric acid/sodium chloride (300 ml, 2×). The ethyl acetate extract was dried over magnesium sulfate, filtered and the ethyl acetate was removed in vacuo to yield 21.88 g of a light yellow foam. This foam was recrystallized from ethyl acetate (approximately 75 ml) to yield 11.6 g of 7-(S)-[D-5-(2,4-dichlorobenzoylamino)-5-carboxylic acid)valeramido]-3-acetoxymethyl-3-cephem-4-carboxylate sulfone: n.m.r.: (DMSOd$_6$) δ 1.5 to 2.4 (m, 6, adipamido methylenes), 2.03 (s, 3, acetoxymethyl), approx. 4.4 (m, 3, C-2 protons and valeramido methine proton), 4.80 (q, 2, 3-methylene protons), 5.20 (dd, 1, $J^{N-H}=8$, $J^{C-6}=2.3$, C-7 proton), 5.48 (d, 1, $J^{C-7}=2.3$, C-6 proton), 7.4 to 7.8 (m, 3, aromatic protons), 8.86 (d, 1, $J^{C-6}=9$, proton of amide at C-7), 9.00 (d, 1, J=5, valeramido 5-amino proton).

EXAMPLE 2

Sodium 7-(S)-(p-toluylamido)-3-acetoxymethyl-3-cephem-4-carboxylate sulfone

A. Epimerization 7-(R)-(p-Toluylamido)-3-acetoxymethyl-3-cephem-4-carboxylic acid sulfone (63.4 g) was slurried in water (1300 ml) and to this slurry an aqueous solution of sodium acetate (13.53 g, 165 mm in 50 ml of water) was added to form a solution. An aqueous solution of piperazine (29.07 g, 337.5 mm in 150 ml of water) was added dropwise to the cephalosporin solution over a twenty-minute period and the resultant reaction mixture was stirred for 5 minutes. The reaction mixture was then cooled to 15° C. and the pH of the reaction mixture was adjusted to 6.04 by the addition of hydrochloric acid. The resultant pale yellow solid was isolated by filtration, washed with water (250 ml), then dried in an air oven at 60° C. for 22 h, yielding 47.2 g of 7-(S)-(p-toluylamido)-3-acetoxymethyl-3-cephem-4-carboxylic acid sulfone (74%).

B. Salt Formation

The above 7-(S)-(p-toluylamido)-3-acetoxymethyl-3-cephem-4-carboxylic acid sulfone was combined with other portions of the same compound (a total of 174.91 g, 414 mm) and then dissolved in methanol (250 ml). Sodium acetate (37.34 g, 455.4 mm) was dissolved in methanol (1500 ml). These two methanol solutions were combined and stirred at room temperature for 1 h. A precipitate was collected by filtration, washed with methanol (400 ml) and dried in an air oven at 60° C. for 24 h, yielding 164.3 g (89%) of sodium 7-(S)-(p-toluylamido)-3-acetoxymethyl-3-cephem-4-carboxylate sulfone: n.m.r. (DMSOd$_6$) δ 2.01 (s, 3, acetoxymethyl protons), 2.37 (s, 3, toluamido methyl protons), 4.00 (q, 2, C-2 methylene protons), 4.53 (q, 2, C-3' methylene protons), 5.35 (d, 1, $J^{C-7}=2.3$, C-6 proton), 5.37 (dd, 1, $J^{C-6}=2.3$, $J^{N-H}=8$, C-7 proton), 7.3 to 7.85 (m, 4, aromatic protons), 9.63 (d, 1, $J^{C-7}=8$, amido proton).

EXAMPLE 3

7-(S)-[2-(Thien-2-yl)-acetamido]-3-acetoxymethyl-3-cephem-4-carboxylic acid sulfone 7-(R)-[2-Thien-2-yl)-acetamido]-3-acetoxymethyl-3-cephem-4-carboxylic acid sulfone (250 mg) was slurried in water (10 ml) and triethylamine (0.16 ml, 114 mg) was added. The reaction mixture was allowed to stir until thin layer chromatographic analysis indicated that the reaction was complete. The reaction mixture was then chilled in an alcohol-ice bath, ethyl acetate (15 ml) was added and the pH of the solution was adjusted to 2.5 by the addition of 1N sulfuric acid. The ethyl acetate layer was then removed and the aqueous solution was extracted with an additional portion of ethyl acetate (15 ml). The ethyl acetate extracts were combined, dried over magnesium sulfate and evaporated to dryness under vacuum at 110° C. to yield 152 mg of 7-(S)-[2-(thien-2-yl) acetamido]-3-acetoxymethyl-3-cephem-4-carboxylic acid sulfone: n.m.r. (CDCl$_3$/DMSO-d$_6$) δ 2.02 (s, 3, acetoxymethyl protons), 3.8 (s, 2, acetamido methylene protons), 3.95 (q, 2, C-2 methylene protons), 4.86 (q, 2, C-3' methylene protons), 5.2 (d, 1, $J^{C-7}=2.3$, C-6 proton), 5.24 (dd, 1, $J^{C-6}=2.3$, $J^{N-H}=8$, C-7 proton), 6.8 to 7.35 (m, 3, aromatic protons), 9.1 (d, 1, $J^{C-7}=8$, amido proton).

EXAMPLE 4

7-(S)-Benzamido-3-acetoxymethyl-3-cephem-4-carboxylic acid sulfone 7-(R)-Benzamido-3-acetoxymethyl-3-cephem-4-carboxylic acid sulfone (46.1 g) was added to water (500 ml) and the pH of the suspension was adjusted to 7 by the addition of 1N sodium hydroxide solution. An aqueous solution of piperazine.6H$_2$O (21.9 g in 600 ml of water) was added to the solution and the reaction mixture was stirred. The progress of the reaction was followed by HPLC analysis and when the reaction was substantially complete (approximately 10 minutes), the pH of the reaction mixture was adjusted to 7.0 by the addition of 1N hydrochloric acid. Ethyl acetate (1500 ml) was added to the reaction mixture and the pH of the resultant solution was adjusted to 2.1 by the addition of 1N hydrochloric acid. The ethyl acetate layer was decanted and the aqueous solution was extracted with additional ethyl acetate (400 ml, 2×). The ethyl acetate layers were combined, washed with acidified saturated aqueous sodium chloride solution (2×), dried over magnesium sulfate, filtered, and evaporated in vacuo. The resultant foam was dissolved in methanol (500 ml) and this solution was allowed to crystallize in the refrigerator for 2.5 h. The crystals were collected by suction filtration, washed with cold methanol, then dried in air to yield 26.9 g (58%) of 7α-benzamido-3-acetoxymethyl-3-cephem-4-carboxylic acid sulfone: n.m.r. (DMSOd$_6$) δ 2.03 (s, 3, acetoxymethyl protons), 4.29 (q, 2, C-2 methylene protons), 4.72 (q, 2, C-3'-methylene protons), 5.30 (dd, 1, $J^{C-6}=2.3$, $J^{N-H}=8$, C-7 proton), 5.59 (d, 1, $J^{C-7}=2.3$, C-6 proton), 7.3 to 8.0 (m, 5, aromatic protons), 9.57 (d, 1, $J^{C-7}=8$, amido proton).

EXAMPLE 5

7-(S)-[2-(Phenoxyacetamido]-3-acetoxymethyl-3-cephem-4-carboxylic acid sulfone 7-(R)-(2-Phenoxyacetamido)-3-acetoxymethyl-3-cephem-4-carboxylic acid sulfone (35 g, 0.076 m) was slurried in water (400 ml) and an aqueous solution of sodium acetate (6.24 g) was added. The solution was stirred for 5 minutes and a 20% aqueous solution of piperazine was added dropwise over a twenty-five-minute period resulting in a pH of 10.0 for the final solution. This solution was stirred for an additional 5 minutes, ethyl acetate (100 ml) then concentrated hydrochloric acid were added to the reaction solution resulting in a pH 5.5. Decolorizing carbon (Darco TM) was added and the solution was suction-filtered using a filter aid (Hyflo). The pH of the filtrate was lowered to 2.0 by the addition of concentrated hydrochloric acid. The layers were separated and the ethyl acetate layer was dried over magnesium sulfate, filtered and evaporated to dryness. The resultant foam was taken up in methanol and the methanol solution was placed in the refrigerator overnight, yielding 5.75 g of 7-(S)-(2-phenoxyacetamido)-3-acetoxymethyl-3-cephem-4-carboxylic acid sulfone: n.m.r. (DMSO-$d_6$) δ 2.01 (s, 3, acetoxymethyl protons), 4.19 (q, 2, C−2 methylene protons), 4.61 (s, 2, acetamido methylene protons), 4.75 (q, 2, C−3' methylene protons), 5.27 (dd, 1, $J^{C-6}=2.3$, $J^{N-H}=8$, C−7 proton), 5.44 (d, 1, $J^{C-7}=2.3$, C−6 proton), 6.8 to 7.4 (m, 5, aromatic protons), 9.24 (d, 1, $J^{C-7}=8$, amido proton).

EXAMPLE 6

7-(S)-Benzylcarbamato-3-acetoxymethyl-3-cephem-4-carboxylic acid sulfone 7-(R)-Benzylcarbamato-3-acetoxymethyl-3-cephem-4-carboxylic acid sulfone (4.4 g) was partially dissolved in water (100 ml) and sodium acetate (0.65 g) was added. An aqueous solution of piperazine (1.6 g in 13 ml of water) was added to this solution first in a small portion (3 ml), then dropwise at the rate of 1 ml every 2 minutes for a twenty-minute period. After addition of the last portion of aqueous piperazine the pH of the resultant solution was 9.5. The progress of the reaction was monitored by HPLC analysis and 35 minutes after addition of the final amount of piperazine, the analysis showed the reaction to be substantially complete. The reaction mixture was chilled by the addition of ice, followed by the addition of cold ethyl acetate (100 ml), while stirring this mixture in an alcohol-ice bath. The pH of the mixture was adjusted to 2.5 by the addition of 12N sulfuric acid, the ethyl acetate layer was removed, and the aqueous layer was again extracted with ethyl acetate. The ethyl acetate extracts were combined, dried over magnesium sulfate, filtered, and the ethyl acetate was removed under vacuum to yield a foam (2.9 g) of 7-(S)-benzylcarbamato-3-acetoxymethyl-3-cephem-4-carboxylic acid sulfone: n.m.r. (DMSO-$D_6$) δ 2.02 (s, 3, acetoxymethyl protons), 4.27 (q, 2, C−2 methylene protons), 4.75 (q, 2, C−3 methylene protons), 5.04 (dd, 1, $J^{C-6}=2.3$, $J^{N-H}=8$, C−7 proton), 5.10 (s, 2, benzylmethylene protons), 5.46 (d, 1, $J^{C-7}=2.3$, C−6 proton), 7.32 (s, 5, aromatic protons), 8.50 (d, 1, $J^{C-7}=8$, amido proton).

EXAMPLE 7

7-(S)-(2-Phenylacetamido)-3-acetoxymethyl-3-cephem-4-carboxylic acid sulfone 7-(R)-(2-Phenylacetamido)-3-acetoxymethyl-3-cephem-4-carboxylic acid sulfone (34 g, 0.076 m) was slurried in water and an aqueous sodium acetate solution (7.38 g, 0.09 m) was added to the slurry. The resultant mixture was stirred for 5 minutes, then a 20% aqueous piperazine solution was added dropwise over a twenty-minute period until the reaction mixture had a pH of 9.9. Upon reaching the pH of 9.9, the reaction mixture was stirred for an additional 5 minutes and ethyl acetate (150 ml) was added. The pH of the mixture was adjusted to 5.5 by the addition of concentrated hydrochloric acid. The acidified solution was treated with decolorizing carbon (Darco TM), filtered, and the filter cake was washed with an ethyl acetate-water solution. The pH of the filtrate was adjusted to 2.0 by the addition of concentrated hydrochloric acid. The ethyl acetate layer was removed and the ethyl acetate layers were combined and dried over magnesium sulfate, filtered, and evaporated in vacuo. The resultant foam was taken up in methanol and precipitated to yield 16.89 g of 7-(S)-(2-(phenylacetamido)-3-acetoxymethyl-3-cephem-4-carboxylic acid sulfone: n.m.r. (DMSO-$d_6$) δ 2.01 (s, 3, acetoxymethyl protons), 3.54 (s, 2, acetamido methylene protons), 4.23 (q, 2, C−2 methylene protons), 4.73 (q, 2, C−3' methylene proton), 5.13 (dd, 1, $J^{C-6}=2.3$, $J^{N-H}=8$, C−7 proton), 5.42 (d, 1, $J^{C-7}=2.3$, C−6 proton), 7.24 (m, 4, aromatic protons), 9.10 (d, 1, $J^{C-7}=8$, amido proton).

We claim:

1. A compound of the formula:

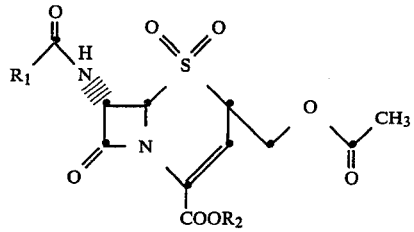

wherein $R_1$ is
- a. $C_1$ to $C_7$ alkyl, $C_3$ to $C_7$ alkenyl, chloromethyl, dichloromethyl, 4-carboxybutyl, 4-formylbutyl, 4-substituted carboxybutyl, 4-amino-4-carboxybutyl, 4-protected amino-4-carboxybutyl, or 4-protected amino-4-substituted carboxybutyl; or
- b. $C_1$ to $C_6$ alkoxy, $C_3$ to $C_6$ cycloalkoxy, benzyloxy or substituted benzyloxy, wherein the substituents are one to three groups chosen from the group consisting of $C_1$ to $C_4$ alkyl, $C_1$ to $C_4$ alkoxy, and chloro; or
- c. 1,4-cyclohexadienyl, phenyl or substituted phenyl, wherein the substituents are one or two groups chosen from the group consisting of chlorine, bromine, hydroxy, protected hydroxy, trifluoromethyl, $C_1$ to $C_4$ alkyl, $C_1$ to $C_4$ alkoxy, carboxy, carboxymethyl, hydroxymethyl, aminomethyl, and protected aminomethyl; or
- d. an arylalkyl group of the formula $$R'-(O)_m-CH_2-$$

wherein R' is 1,4-cyclohexadienyl, phenyl or substituted phenyl as defined above, and m is zero or one; or
e. a substituted arylalkyl group of the formula

wherein R'' is R' as defined above, 2-thienyl, or 3-thienyl; W is hydroxy or protected hydroxy, carboxy or protected carboxy, amino or protected amino; or
f. a heteroarylmethyl group of the formula

R'''—CH$_2$— wherein R''' is 2-thienyl, 3-thienyl, 2-furyl, 3-furyl, 2-thiazolyl, 5-tetrazolyl or 1-tetrazolyl; and
$R_2$ is hydrogen, the conjugate acid of a nitrogen base that has a pKa between about 9.0 to about 11.5, sodium or potassium ion.

2. A compound of claim 1, wherein $R_2$ is sodium, potassium, hydrogen, benzylammonium, methylammonium, trimethylammonium, dimethylammonium, n-butylammonium, cyclohexylammonium, ethylammonium, triethylammonium, diethylammonium, diisopropylammonium, hexamethylenediamine, ethylenediamine, and piperazinium.

3. A compound of claim 2, wherein $R_1$ is $C_1$–$C_7$ alkyl, $C_3$–$C_7$ alkenyl, halomethyl, 4-carboxybutyl, 4-butyraldehyde, 4-substituted carboxybutyl, 4-amino-4-carboxybutyl, 4-protected amino-4-carboxybutyl, or 4-protected amino-4-substituted carboxybutyl.

4. A compound of claim 3, wherein $R_1$ is 4-protected amino-4-carboxybutyl.

5. A compound of claim 4, wherein $R_1$ is 4-(2,4-dichlorobenzyloxycarbonylamino)-4-carboxybutyl.

6. A compound of claim 5, wherein $R_2$ is sodium or hydrogen.

7. A compound of claim 2, wherein $R_1$ is $C_1$–$C_6$ alkoxy, $C_3$–$C_6$ cycloalkoxy, benzyloxy or substituted benzyloxy, wherein the substituents are 1 to 3 groups chosen from the group consisting of $C_1$–$C_4$ alkyl, $C_1$–$C_4$ alkoxy, and chloro.

8. A compound of claim 7, wherein $R_1$ is benzyloxy.

9. A compound of claim 8, wherein $R_2$ is sodium or hydrogen.

10. A compound of claim 2, wherein $R_1$ is 1,4-cyclohexadienyl, phenyl or substituted phenyl, wherein the substituents are 1 or 2 groups chosen from the group consisting of chlorine, bromine, hydroxy, protected hydroxy, trifluoromethyl, $C_1$–$C_4$ alkyl, $C_1$–$C_4$ alkoxy, carboxy, carboxymethyl, hydroxymethyl, aminomethyl, and protected aminomethyl.

11. A compound of claim 10, wherein $R_1$ is phenyl or p-methylphenyl.

12. A compound of claim 11, wherein $R_2$ is sodium or hydrogen.

13. A compound of claim 2, wherein $R_2$ is an arylalkyl group of the formula

R'—(O)$_m$—CH$_2$— wherein R' is phenyl or substituted phenyl, and m is 0 or 1.

14. A compound of claim 13, wherein $R_1$ is phenyl.

15. A compound of claim 14, wherein $R_2$ is sodium or hydrogen.

16. A compound of claim 2, wherein $R_1$ is a heteroarylmethyl group of the formula

R'''—CH$_2$—.

17. A compound of claim 16, wherein R''' is 2-thienyl.

18. A compound of claim 17, wherein $R_2$ is triethylammonium or hydrogen.

19. A process for preparing a compound of claim 1, which comprises reacting in an aqueous medium at a pH between about 9.0 and about 11.5 a 7-(R)-acylaminocephalosporin sulfone compound of the formula

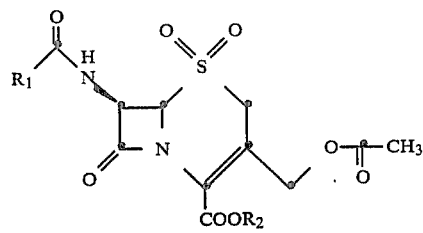

with an organic nitrogen base having a pKa between about 9.0 to about 11.5 at a temperature between about 0° C. to about 40° C.

20. A process of claim 19, wherein the organic nitrogen base is benzylamine, methylamine, trimethylamine, dimethylamine, n-butylamine, cyclohexylamine, ethylamine, triethylamine, diethylamine, diisopropylamine, hexamethylenediamine, ethylenediamine, or piperazine.

21. A process of claim 20, wherein $R_2$ is sodium, potassium, hydrogen, benzylammonium, ethylammonium, trimethylammonium, dimethylammonium, n-butylammonium, cyclohexylammonium, ethylammonium, triethylammonium, diethylammonium, diisopropylammonium, hexamethylenediammonium, hexamethylenediamine, ethylenediamine, and piperazinium.

22. A process of claim 21, wherein the process is carried out at a pH between about 9.5 to about 10.5.

23. A process of claim 22, wherein the process is carried out at a temperature between about 15° C. to about 25° C.

24. A process of claim 23, wherein the organic nitrogen base is triethylamine or piperazine.

25. A process of claim 24, wherein $R_1$ is $C_1$–$C_7$ alkyl, $C_3$–$C_7$ alkenyl, chloromethyl, dichloromethyl, 4-carboxybutyl, 4-formylbutyl, 4-substituted carboxybutyl, 4-amino-4-carboxybutyl, 4-protected amino-4-carboxybutyl, or 4-protected amino-4-substituted carboxybutyl.

26. A process of claim 25, wherein $R_1$ is 4-protected amino-4-carboxybutyl.

27. A process of claim 26, wherein $R_1$ is 4-(2,4-dichlorobenzyloxycarbonylamino)-4-carboxybutyl.

28. A process of claim 27, wherein $R_2$ is sodium.

29. A process of claim 24, wherein $R_1$ is $C_1$–$C_6$ alkoxy, $C_3$–$C_6$ cycloalkoxy, benzyloxy or substituted benzyloxy, wherein the substituents are 1 to 3 groups chosen from the group consisting of $C_1$–$C_4$ alkyl, $C_1$–$C_4$ alkoxy, and chloro.

30. A process of claim 29, wherein $R_2$ is benzyloxy.
31. A process of claim 30, wherein $R_1$ is sodium.
32. A process of claim 24, wherein $R_1$ is 1,4-cyclohexadienyl, phenyl or substituted phenyl, wherein the substituents are 1 or 2 groups chosen from the group consisting of chlorine, bromine, hydroxy, protected hydroxy, trifluoromethyl, $C_1$–$C_4$ alkyl, $C_1$–$C_4$ alkoxy, carboxy, carboxymethyl, hydroxymethyl, aminomethyl, and protected aminomethyl.
33. A process of claim 32, wherein $R_1$ is phenyl or p-methylphenyl.
34. A process of claim 33, wherein $R_2$ is sodium.
35. A process of claim 24, wherein $R_1$ is an arylalkyl group of the formula $$R'-(O)_m-CH_2-$$

wherein $R'$ is 1,4-cyclohexadienyl, phenyl or substituted phenyl as defined above, and m is 0 or 1.
36. A process of claim 25, wherein $R_1$ is phenyl.
37. A process of claim 36, wherein $R_1$ is sodium.
38. A process of claim 24, wherein $R_1$ is a heteroarylmethyl group of the formula $$R'''-CH_2-$$

wherein $R'''$ is 2-thienyl, 3-thienyl, 2-furyl, 3-furyl, 2-thiazolyl, 5-tetrazolyl, or 1-tetrazolyl.
39. A process of claim 38, wherein $R_1$ is 2-thienyl.
40. A process of claim 39, wherein $R_2$ is triethylammonium.

* * * * *